United States Patent [19]

Wagner

[11] 4,067,998
[45] Jan. 10, 1978

[54] 2-((3,5-DI-TERT-BUTYLPHENYL)THIO) ALKANOIC ACIDS AND DERIVATIVES

[75] Inventor: Eugene R. Wagner, Midland, Mich.

[73] Assignee: The Dow Chemical Company, Midland, Mich.

[21] Appl. No.: 549,613

[22] Filed: Feb. 13, 1975

Related U.S. Application Data

[63] Continuation of Ser. No. 441,617, Feb. 11, 1974, abandoned, which is a continuation-in-part of Ser. No. 332,322, Feb. 14, 1973, abandoned.

[51] Int. Cl.$^2$ .................. A61K 31/19; C08H 3/00; C07C 149/40
[52] U.S. Cl. .................................. 424/317; 260/399; 260/516; 260/501.21; 424/308; 560/17
[58] Field of Search ............... 260/473 G, 470, 516, 260/399; 424/308, 317

[56] References Cited

U.S. PATENT DOCUMENTS

| 2,017,613 | 10/1935 | Veraguth et al. | 260/516 |
| 2,215,367 | 9/1940 | Balle et al. | 260/516 |
| 2,880,137 | 3/1959 | Elson | 260/470 |
| 3,098,078 | 7/1963 | Druey et al. | 260/327 |
| 3,262,850 | 7/1966 | Jones et al. | 260/473 G |
| 3,383,411 | 5/1968 | Schultz | 260/470 |
| 3,392,194 | 7/1968 | Warning | 260/516 |
| 3,426,067 | 2/1969 | Weber et al. | 260/470 |
| 3,448,149 | 6/1969 | Aumüller et al. | 260/470 |
| 3,494,957 | 2/1970 | Naganishi et al. | 260/473 G |
| 3,549,691 | 12/1970 | Leigh et al. | 260/473 G |
| 3,652,646 | 3/1972 | Leigh et al. | 260/473 G |
| 3,674,836 | 7/1972 | Creger et al. | 260/473 G |

OTHER PUBLICATIONS

Kuliev et al., Chem. Abstracts, vol. 67, 63972(x), 1967,
Seidel et al., Chem. Abstracts, vol. 51, 2622(c), 1957.

*Primary Examiner*—James O. Thomas, Jr.
*Assistant Examiner*—G. T. Breitenstein
*Attorney, Agent, or Firm*—Maynard R. Johnson; Daniel L. DeJoseph

[57] ABSTRACT

2-((3,5-Di-tert-butylphenyl)thio) alkanoic acids and ester derivatives and pharmaceutically-acceptable salts thereof are disclosed; pharmaceutical compositions containing said compounds and methods of reducing plasma lipid levels in mammals are also provided.

35 Claims, No Drawings

2-((3,5-DI-TERT-BUTYLPHENYL)THIO) ALKANOIC ACIDS AND DERIVATIVES

CROSS-REFERENCE TO RELATED APPLICATION

This is a continuation of application Ser. No. 441,617 filed Feb. 11, 1974, now abandoned, which is a continuation-in-part of application Ser. No. 332,322, filed Feb. 14, 1973, now abandoned.

BACKGROUND OF THE INVENTION

This invention relates to novel 2-((3,5-di-tert-butylphenyl)thio) alkanoic acids and ester derivatives thereof (hereinafter referred to, for convenience, as "alkanoic acids"). This invention also relates to methods and compositions for reducing plasma lipid levels, especially cholesterol and triglycericide levels and, in particular, triglyglyceride levels.

As established by various studies, it is recognized that cholesterol and triglycerides play a major role in the formation of atherosclerotic plaques by accelerating the deposition of blood lipids in the arterial wall. It has been discovered that representative compounds of the group herein disclosed are effective in reducing cholesterol levels, and particularly triglyceride levels in the blood of mammals. These activities make the compounds herein useful as compositions in ameliorating such conditions as atherosclerosis and other clinical entities in which the underlying etiology is associated with lipid imbalance or hyperlipidemia.

BRIEF SUMMARY OF THE INVENTION

The alkanoic acids and derivatives with which the present invention is concerned are represented by the general formula:

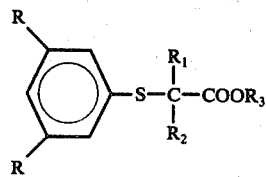

wherein:
each R represents a tert-butyl group;
$R_1$ represents hydrogen or methyl;
$R_2$ represents an alkyl group of from one to about six carbon atoms;
$R_3$ represents hydrogen or an alkyl group of from one to about three carbon atoms; or
the salts thereof formed with pharmaceutically acceptable bases.

DETAILED DESCRIPTION OF THE INVENTION

In general, any base which will form an acid addition salt with a carboxylic acid and whose pharmacological properties will not cause an adverse physiological effect when ingested by the body system is considered as being within the scope of this invention. Suitable bases thus include, for example, the alkali metal and alkaline earth metal hydroxides, carbonates, bicarbonates, etc., such as sodium hydroxide, potassium hydroxide, calcium hydroxide, potassium carbonate, sodium bicarbonate, magnesium carbonate and the like, ammonia, primary, secondary and tertiary amines and the like. Also, aluminum salts of the instant compounds may be obtained by treating the corresponding sodium salt with an appropriate aluminum complex such as aluminum chloride hexahydrate, etc. The acid addition salts thus obtained are the functional equivalent of the corresponding alkanoic acids and one skilled in the art will appreciate that the variety of acid addition salts embraced by this invention are limited only by the criterion that the bases employed in forming the salts be both non-toxic and physiologically acceptable.

The term "alkyl" as used in the specification and claims means both straight and branched chain alkyl radicals containing from 1 to about 6 carbon atoms, e.g., methyl, ethyl, propyl, isopropyl, butyl, isobutyl, t-butyl, amyl, hexyl and the like.

Preferred compounds of the above formula include those wherein $R_1$ is hydogen. In still another embodiment, preferred compounds include those wherein $R_3$ is hydrogen. Still another preferred class of compounds includes those wherein $R_2$ is selected from the group consisting of methyl, n-propyl, n-butyl and n-pentyl. A further preferred class of compounds include those wherein $R_3$ is alkyl. Another preferred class of compounds includes those wherein $R_1$ is methyl, $R_2$ is methyl, n-propyl or n-pentyl, and $R_3$ is hydrogen.

The compounds of the present invention can be prepared by reacting a 3,5-di-t.-butylmercaptophenol of the formula:

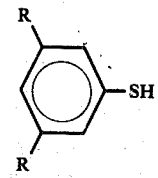

with a selected haloalkanoic acid or alkanoate reactant of the formula:

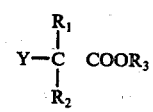

wherein, in the above formulas, Y is halogen, such as bromo or chloro, and each of R, $R_1$, $R_2$ and $R_3$ are as previously defined. The reaction is ordinarily carried out in the presence of an inert liquid reaction medium, such as, for example, methanol, ethanol, propanol, t-butanol, benzene, dimethylformamide, toluene or the like, and a base, such as, for example, alkali metal and alkaline earth hydroxides, carbonates and the like. Representative of such bases are sodium hydroxide, potassium hydroxide, calcium hydroxide, potassium carbonate and the like. For compounds wherein $R_3$ is hydrogen, i.e., the acid derivatives, a ratio of about two moles of base per mole of phenol reactant is usually employed while equimolar amounts of base and phenol reactant are usually employed for compounds wherein $R_3$ is alkyl. Generally, equimolar amounts of the phenol and alkanoic acid or alkanoate reactants are employed.

In preparing compounds wherein $R_3$ is alkyl, the mercapto phenol reactant is usually dispersed in a selected reaction medium and a solution of base added slowly thereto with stirring. During the base addition, the reaction mixture is usually cooled. Following the completion of the base addition, the alkanoic acid or alkanoate reactant is added to the reaction mixture and the resulting reaction mixture, which warms slightly due to exothermic reaction, is usually maintained, with stirring, at ambient temperatures for a period of from about 4 to 24 or more hours in order to allow for substantial completion of the reaction. Upon completion of the reaction period, the reaction mixture is acidified with aqueous hydrochloric acid and stirred. The resulting product precipitate, which is obtained by filtration of the reaction mixture, is washed with water and dried. The dried precipitate can be further purified if desired by recrystallizing the same from a suitable solvent such as, for example, ethanol, methylene chloride, hexane, chloroform or the like.

Compounds wherein $R_3$ is hydrogen are conveniently obtained by hydrolyzing with excess base the compounds wherein $R_3$ is alkyl (i.e., the alkanoate products).

In such procedures, the alkanoate product is mixed with ethanol and a base as hereinbefore described and the resulting reaction mixture allowed to boil on a steam bath for a period of from about 1 to about 3 or more hours. The reaction mixture is then acidified as set forth above and the resulting oily layer or gummy precipitate thus formed is extracted with a suitable solvent, e.g., methylene chloride, ethyl acetate or the like, and the extract or extracts combined and washed with water. The extract is dried and reduced by evaporation to obtain the desired alkanoic acid product as an oily liquid or crystalline solid which can be further purified according to conventional techniques such as distillation, recrystallization and the like. Substantial amounts of the desired alkanoic acid products can be obtained by employing excess amounts of base in the reaction of the 3,5-di-t-butylmercaptophenol reactant with an appropriate haloalkanoic acid reactant if desired.

The compounds of the present invention exhibit valuable pharmacological properties useful in the chemotherapeutic treatment of disorders and conditions associated with lipid imbalance or hyperlipidemia. Thus, in one embodiment of the present invention, methods of ameliorating conditions associated with hyperlipidemia are provided. In this respect, it has been discovered that many compounds of the class herein described exhibit hypocholesterolemic activity as well as unusually high hypotriglyceridemic activity. Such pronounced hypotriglyceridemic activity thus renders such compounds particularly useful in the chemotherapeutic treatment of pathological states characterized by high glyceride levels, i.e., hypertriglyceridemia. Thus, in another embodiment of the present invention, methods of treating hypertriglyceridemia are also provided.

For oral administration, pharmaceutical preparations of this invention may be made by following the conventional techniques of the pharmaceutical chemist. These techniques invole granulating and compressing when necessary or variously mixing and dissolving or suspending the ingredients as appropriate to the desired end product. Numerous pharmaceutical forms to carry the compounds can be used. For example, the pure compound can be used or it can be mixed with a solid carrier. Generally, inorganic pharmaceutical carriers are preferable and particularly solid inorganic carriers. One reason for this is the large number of inorganic materials which are known to be pharmaceutically safe and acceptable, as well as very convenient in preparing formulations. The compositions may take the form of tablets, linguets, powders, capsules, slurries, troches or lozenges and such compositions may be prepared by standard pharmaceutical techniques. Tablet compositions may be coated or uncoated and they may be effervescent or non-effervescent. Conventional excipients for tablet formations may be used. For example, inert diluents, such as magnesium carbonate or lactose, disintegrating agents such as maize starch or alginic acid, and lubricating agents such as magnesium stearate may be used.

If a liquid carrier is used, the preparation may be in the form of a soft gelatin capsule, a syrup, a liquid solution or suspension.

The hydrocarbon solubility of most of the compounds of this invention is high enough to allow the use of pharmaceutically-acceptable oils as carriers. For example vegetable or animal oils such as sunflower oil, safflower oil, maize oil or codliver oil can be used. Glycerine can also be used. With this latter solvent, from 2 to 30 percent water may be adeed. When water alone is the carrier, or when the solubility of the compound in the oil is low, the preparations can be administered in the form of a slurry.

Emulsion compositions may be formulated using emulsifying agents such as sorbitan tri-oleate, polyoxyethylene sorbitan monooleate, lecithin, gum acacia or gum tragacanth. Aqueous bases suspensions may be prepared with the aid of wetting agents such as polyethylene oxide condensation products of alkylphenols, fatty alcohols or fatty acids with the suspending agents, for example a hydrophilic colloid such as polyvinylpyrolidone. The emulsions and suspensions may contain conventional excipients such as sweeting agents, flowing agents, coloring materials and preservatives.

The compounds of this invention can also be incorporated in a nutritive foodstuff such as, for example, butter, margarine, edible oils, casein, carbohydrates and the like. Such nutritive compositions are adapted to be administered as a partial or total diet or as a supplement to the diet. Such compositions preferably contain from about 0.02 or less to about 2.0 or more percent of the active ingredient when administered as the total diet. The compositions can contain higher concentrations of the active ingredient when administered as a supplement.

For parenteral use, the compounds of this invention can be formulated with sterile ingredients, compounded and packaged asceptically. They may be administered intravenously or intramuscularly. Useful solvents for formulation in such use are the polyhydric aliphatic alcohols and mixtures thereof. Especially satisfactory are the pharmaceutically acceptable glycols, such as propylene glycol, and mixtures thereof. Glycerine is another example of a polyol which is particularly useful. Up to 25–30 percent by volume of water may be incorporated in the vehicle if desired. An 80 percent aqueous propylene glycol solution is a particularly convenient solvent system. A pH range, about 7.4, and isotonicity compatible with body isotonicity, is desirable. Basicity may be controlled by addition of a base as required, and a particularly convenient base is monoethanolamine. It may often be desirable to incorporate a local anaesthetic and such are well known to those skilled in the art.

The percentage of the compound to be used in the pharmaceutical carrier may be varied. It is necessary that the compound constitute a proportion such that a suitable dosage will be obtained and it is preferred to use pharmaceutical compositions containing at least 10 weight percent of the compound. Activity increases with concentration of the agent in the carrier, but those compositions containing a significant amount of carrier, e.g. at least 1 percent and preferably at least 5 percent, are preferred as they allow for the easier administration of the compound.

Generally, an effective daily dosage of the active ingredient can be from less than about 1 to about 100 milligrams or more per kilogram (mg./kg.) of body weight for most mammals. Dosage unit forms usually contain from about 1 to about 1000 mg., usually from about 1 to about 500 mg. of an active compound. One or more unit dosage forms are administered internally to a mammal to provide an active compound daily dosage level of from about 1 to about 4000 mg. or more.

However, it is not intended that the dosage regimens of the compounds or compositions be limited to any particular range. The dosage range desired in this invention is that range necessary to accomplish the desired end of lowering serum lipid levels. The amount of lipid level reduction desired will not be the same in all instances, but depends upon such factors as initial lipid level, predominance of one form of lipid over another, etc. The dosage, whether oral or parenteral must, therefore, of necessity be individually determined. Likewise, the concentration range of the compounds in the various formulations of this invention is not limited. The concentration should be high enough to avoid any excessive number of administrations per day, but low enough to allow flexibility in administration.

The active acid compound and/or their corresponding esters or salts may be administered. In addition, other complementary hypolipidemic, hypocholesteremic or hypoglycemic agents as well as vitamins, analgesics, androgens, and the like compatible with the present compounds can be included in the present formulations to secure advantageous combination therapy. Moreover, preservatives, stabilizers, wetting agents, buffers, and the like can be incorporated, if desired, into the above formulations. Additionally, the formulations may also contain other therapeutically valuable substances.

The term "unit dosage form" as used in the specification and claims herein refers to physically discrete units suitable as unitary dosages, each unit containing a predetermined quantity of active material calculated to produce the desired therapeutic effect in association with the required pharmaceutical diluent, carrier or vehicle. The specification for the novel unit dosage forms of this invention is dictated by and directly dependent on (a) the unique characteristics of the active material and the particular therapeutic effect to be achieved and (b) the limitations inherent in the art of compounding such an active material for therapeutic use, as disclosed in detail in this specification, these being features of the present invention.

The invention will be more fully understood from the examples which follow. These examples are illustrative of the invention and are not to be construed as limiting the same.

EXAMPLE 1

3,5-Di-t-butylmecaptophenol (22.2 grams; 0.1 mole) was added to a stirred solution of sodium hydroxide (4.0 grams; 0.1 mole) in 125 ml. of 95% ethanol. To this mixture, ethyl 2-bromoisobutyrate (19.5 grams; 0.1 mole) was added and the resulting reaction mixture was stirred at ambient temperatures for a period of about 24 hours. The reaction mixture was subsequently poured into an aqueous 5% HCl solution with stirring. The oily layer formed upon acidification was separated from the reaction mixture and extracted with ehtyl acetate, washed with water and dried over sodium sulfate. The extract was evaporated to obtain a light yellow oil representing the desired ethyl 2-((3,5-di-tert-butylphenyl)-thio)-2-methyl-propionate product. Analysis calculated for $C_{20}H_{32}O_2S$: C, 71.38; H, 9.58; S, 9.53. Found: C, 70.55; H, 9.63; S, 9.01.

20 Grams of the product thus obtained was mixed with 100 ml. of a 5N potassium hydroxide solution and 100 ml. of ethanol and the resulting reaction mixture was allowed to boil on a steam bath for a period of about 2 hours. The reaction mixture was then poured into a 10% HCl-ice water mixture and the resulting precipitate collected by filtration. The precipitate thus obtained was extracted with methylene chloride and the extract washed with a brine solution. The aqueous phase was also extracted with methylene chloride. The extracts were combined and washed twice with portions of water and dried over anhydrous sodium sulfate. The solvent was reduced by evaporation and the resulting crystalline precipitate recovered and recrystallized from a benzenepetroleum ether mixture. As a result of these operations, the desired 2-((3,5-di-tert-butylphenyl)thio)-2-methyl propanioc acid product was recovered as a crystalline solid having a melting point of 115°—116° C. was recovered. Analysis calulated for $C_{18}H_{28}O_2S$: C, 70.08; H, 9.15; S, 10.39. Found: C, 70.47; H, 9.17; S, 10.29.

In accordance with the procedures and teachings of Example 1 above, the following alkanoic acid and ester compounds can be prepared by employing the corresponding haloalkanoate reactants and, in the instances of salts, further reaction with the corresponding bases:

ethyl 2-((3,5-di-tert-butylphenyl)thio)-butyrate;
ethyl 2-((3,5-di-tert-butylphenyl)thio)-hexanoate;
ethyl 2-((3,5-di-tert-butylphenyl)thio)-heptanoate;
propyl 2-((3,5-di-tert-butylphenyl)thio)-octanoate;
methyl 2-((3,5-di-tert-butylphenyl)thio)-propionate;
ethyl 2-((3,5-di-tert-butylphenyl)thio)-2-methyl-pentanoate;
methyl 2-((3,5-di-tert-butylphenyl)thio)-2-methyl-propionate;
propyl 2-((3,5-di-tert-butylphenyl)thio)-2-methyl-butyrate;
ethyl 2-((3,5-di-tert-butylphenyl)thio)-2-methyl-octanoate;
propyl 2-((3,5-di-tert-butylphenyl)thio)-2-methyl-hexanoate;
2-((3,5-di-tert-butylphenyl)thio)-hexanoic acid (melting at 90°–91° C.);
2-((3,5-di-tert-butylphenyl)thio)-2-methyl-pentanoic acid (melting at 116°–118° C.);
2-((3,5-di-tert-butylphenyl)thio)-2-methyl-heptanoic acid (melting at 97°–99° C.);
2-((3,5-di-tert-butylphenyl)thio)-b 2-methyl-hexanoic acid (melting at 101°–103° C.);
2-((3,5-di-tert-butylphenyl)thio)-propanoic acid:
2-((3,5-di-tert-butylphenyl)thio)-octanoic acid;
ethyl 2-((3,5-di-tert-butylphenyl)thio)-2-methyl-octanoate;
2-((3,5-di-tert-butylphenyl)thio)-2-methyl-octanoic acid (melting at 79°–81° C.);
2-((3,5-di-tert-butylphenyl)thio)-butyric acid;
2-((3,5-di-tert-butylphenyl)thio-heptanoic acid;
sodium 2-((3,5-di-tert-butylphenyl)thio)-2-methyl-propionate;

potassium 2-((3,5-di-tert-butylphenyl)thio)-2-methyl-octanoate; and calcium 2-((3,5-di-tert-butylphenyl)thio)-2-methyl-heptanoate.

The hypolipidemic effect of the compounds of the invention is illustratively demonstrated in rats. In such procedures, the active test compound is dissolved in acetone, taken up on silica gel, and trtturated with various aliquots of powdered feed until the desired concentration is reached. The feed mixture is then thoroughly mixed and fed to test groups of rats for period of 14 days. Control groups of rats are similarly fed with untreated feed. Following the 14 day feeding period, the rats are sacrificed and the relative levels of serum cholesterol in blood samples determined by the Henly method (A. A. Henly, *Analyst* 82, 286 (1957)). The relative levels of triglyceride levels in blood samples are determined by the Van Handel and Zilversmit method (*J. Lab. Clin. Medl;* 50: 152 (1957) *Clin. Chem.*, 7, 249 (1961). Taking the average levels of the control mammals as standard, the mean results obtained in the treated groups is thereby ascertained.

The data presented in the following Table I indicate the mean decrease in serum cholesterol and serum triglyceride levels, as compared with the average levels of control mammals, obtained by separately feeding groups of rats medicated feeds containing 0.25% by weight of each of the indicated compounds for a period of about 14 days:

Table I

Decrease in Serum Lipid Levels with Feeds Containing 0.25% Active Ingredient

| Compound | Percent Decrease After 14 Days | |
|---|---|---|
| | Cholesterol | Triglyceride |
| 1. 2-((3,5-di-tert-butylphenyl)thio)-hexanoic acid | 21 | 40 |
| 2. 2-((3,5-di-tert-butylphenyl)thio)-2-methyl-propionic acid | 32 | 65 |
| 3. 2-((3,5-di-tert-butylphenyl)thio)-2-methyl-pentanoic acid | 28 | 82 |
| 4. 2-((3,5-di-tert-butylphenyl)thio)-2-methyl-heptanoic acid | 28 | 74 |

The data presented in Table I clearly establish the effectiveness and usefulness of such compounds in treating hyperlipidemia in the blood of a mammal. Such data also show the pronounced hypotriglyceridemic effect of such compounds and the usefulness thereof in instances where predominantly high triglyceride levels exist.

The active compounds of the present invention are preverably administered orally. One or more unit dosage forms may be required for each internal administration, whether enteral or parenteral. The following examples illustrate the preparation of pharmaceutical compositions for hypolipidemic uses or hypotriglyceridemic uses, but are by no means the sole methods of producing the same.

EXAMPLE 2

1,000 Capsules for oral administration, each containing 100 mg. of active ingredient can be prepared from the following ingredients:

| | Grams |
|---|---|
| 2-((3,5-di-tert-butylphenyl)-thio)hexanoic acid | 100 |
| Lactose, U.S.P. | 100 |
| Starch, U.S.P. | 30 |
| Talc, U.S.P. | 6.5 |
| Calcium Stearate | 2.5 |

The active ingredient is powered and mixed with the starch-lactose mixture followed by the talc and calcium stearate. The final mixture is then encapsulated in the usual manner employing hard gelatin capsules of appropriate size.

EXAMPLE 3

2,000 Tablets for oral use, each containing 1,000 mg. of active ingredient are prepared from the following ingredients:

| | Grams |
|---|---|
| 2-((3,5-di-tert-butylphenyl)-thio)-2-methyl-propionic acid | 2000 |
| Starch, U.S.P. | 140 |
| Talc, U.S.P. | 100 |
| Calcium Stearate | 14 |

The active ingredient is powered and granulated with a 4% w/v aqueous solution of methylcellulose U.S.P. (1500 cps.). To the dried granules is added a mixture of the remainder of the ingredients and the final mixture slugged. The slugs are broken down by forcing through a screen and the resulting granules then compressed into tablets of proper weight.

EXAMPLE 4

An injectable preparation is made from the following ingredients to contain 100 mg. of the 2-((3,5-di-tert-butylphenyl)thio)pentanoic acid active ingredient per ml:

| | Percent w/v |
|---|---|
| Sodium carboxymethylcellulose (low viscosity) | 0.5 |
| Tween 80 (polyoxyethylene sorbitan monooleate) | 0.4 |
| Sodium chloride | 0.9 |
| Benzyl alcohol | 0.9 |
| Active ingredient | 10.0 |
| Sterile distilled water, q.s., 1000.0 ml. | |

The previously sterilized active ingredient is homogenized with the already mixed and sterilized vehicle.

The 3,5-di-tert-butyl-mercaptophenol and haloalkanoate reactants are known and are readily available or can be prepared according to known or analogous procedures. For example, M. S. Newman and H. A. Karnes, *J. Org. Chem.*, 31, 3980 (1966) described the preparation of the 3,5-di-tert-butyl-mercaptophenol reactant.

I claim:

1. A compound of the formula:

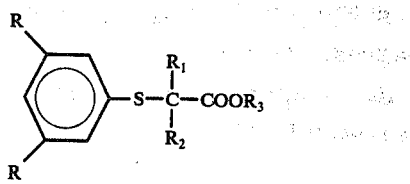

wherein
- each R represents a 1,1-dimethylethyl group;
- R₁ is hydrogen or methyl;
- R₂ represents an alkyl group containing from 1 to about 6 carbon atoms; and
- R₃ represents hydrogen or an alkyl group containing from 1 to about 3 carbon atoms; and the salts thereof formed with pharmaceutically-acceptable bases.

2. A compound as defined in claim 1 wherein R₃ is hydrogen.

3. The pharmaceutically-acceptable salt of a compound as defined in claim 2 with a base.

4. A compound as defined in claim 1 wherein R₃ is alkyl.

5. A compound as defind in claim 2 wherein R₁ is hydrogen.

6. A compound as defined in claim 1 wherein R₂ is selected from the group consisting of methyl, n-propyl, n-butyl and n-pentyl.

7. A compound as defined in claim 1 wherein R₁ is methyl, R₂ is methyl, n-propyl or n-pentyl and R₃ is hydrogen.

8. The compound of claim 1 which is 2-((3,5-di-tert-butylphenyl)thio)hexanoic acid.

9. The compound of claim 1 which is 2-((3,5-di-tert-butylphenyl)thio)-2-methyl-propionic acid.

10. The compound of claim 1 which is 2-((3,5-di-tert-butylphenyl)thio)-b 2-methyl-pentanoic acid.

11. The compound of claim 1 which is 2-((3,5-di-tert-butylphenyl)thio)-2-methyl-heptanoic acid.

12. A composition comprising a hypolipidemically effective amount of a compound of the formula:

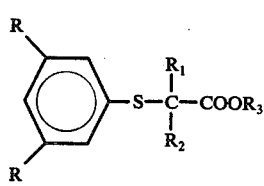

wherein
- each R represents a 1,1-dimethylethyl group;
- R₁ is hydrogen or methyl;
- R₂ represents an alkyl group containing from 1 to about 6 carbon atoms; and
- R₃ represents hydrogen, or a salt thereof formed with pharmaceutically-acceptable base in combination with a pharmaceutical carrier therefor.

13. The composition of claim 12 wherein R₁ is hydrogen.

14. The composition of claim 12 wherein R₁ is methyl.

15. The composition of claim 12 wherein R₂ is selected from the group consisting of methyl, n-propyl, n-butyl and n-pentyl.

16. The composition of claim 15 wherein the compound is 2-((3,5-di-tert-butylphenyl)thio)hexanoic acid.

17. The composition of claim 15 wherein the compound is 2-((3,5-di-tert-butylphenyl)thio)-2-methyl-propionic acid.

18. The composition of claim 15 wherein the compound is 2-((3,5-di-tert-butylphenyl)thio)-b 2-methyl-pentanoic acid.

19. The composition of claim 15 wherein the compound is 2-((3,5-di-tert-butylphenyl)thio)-2-methyl-heptanoic acid.

20. A method for treating hyperlipidemia in the blood of a mammal comprising admisistering internally to said mammal on effective amount of a compound of the formula:

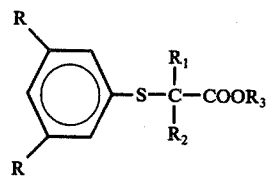

wherein
- each R represents a 1,1-dimethylethyl group;
- R₁ is hydrogen or methyl;
- R₂ represents an alkyl group containing from 1 to about 6 carbon atoms; and
- R₃ represents hydrogen, and the salts thereof formed with acceptable bases, in combination with a pharmaceutical carrier.

21. A method as in claim 20 wherein R₁ is hydrogen.

22. A method as in claim 20 whereon R₃ is alkyl.

23. A method as in claim 20 wherein R₃ ₁ is hydrogen.

24. A method as in claim 20 wherein R₂ is selected from the group consisting of methyl, n-propyl, n-butyl and n-pentyl.

25. A method as in claim 20 wherein the compound is administered orally.

26. The method of claim 24 wherein the compound is 2-((3,5-di-tert-butylphenyl)thio)hexanoic acid.

27. The method of claim 24 wherein the compound is 2-((3,5-di-tert-butylphenyl)thio)-2-metyl-propanoic acid.

28. The method of claim 24 wherein the compound is 2-((3,5-di-tert-butyphenyl)thio)-2-methyl-pentanoic acid.

29. The method of claim 24 wherein the compound is 2-((3,5-di-tert-butylphenyl)thio)heptanoic acid.

30. A method of treating hypertriglyceridemia in the blood of a mammal comprising administering internally to said mammal an effective amount of a compound of the formula:

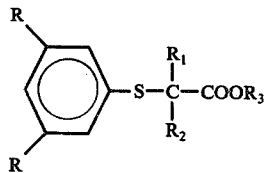

wherein
- each R represents a 1,1-dimethylethyl group;
- R₁ is hydrogen or methyl;
- R₂ represents an alkyl group containing from 1 to about 6 carbon atoms; and $R_3$ represents hydrogen, and the salts thereof formed with pharmaceutically-acceptable bases, in combination with a pharmaceutical carrier.

31. The method of claim 30 wherein $R_1$ is hydrogen.
32. The method of claim 30 wherein $R_3$ is alkyl.
33. The method of claim 30 wherein $R_3$ is hydrogen.
34. The method of claim 30 wherein $R_2$ is selected from the group consisting of methyl, n-propyl, n-butyl and n-pentyl.
35. The method of claim 30 wherein the compound is administered orally.

UNITED STATES PATENT AND TRADEMARK OFFICE
CERTIFICATE OF CORRECTION

PATENT NO. : 4,067,998             Page 1 of 3
DATED : January 10, 1978
INVENTOR(S) : Eugene R. Wagner It is certified that error appears in the above-identified patent and that said Letters Patent are hereby corrected as shown below:

Title Page under "References Cited", seventh reference "Warning" should read -- Waring --;

Title Page under "References Cited", tenth reference "Naganishi et al." should read -- Nakanishi et al. --;

Column 2, line 16, "hydogen" should read --hydrogen--;

Column 2, line 21, "include" should read --includes--;

Column 3, line 55, "invole" should read --involve--;

Column 4, line 18, "adeed" should read --added--;

Column 4, line 25, "bases" should read --based--;

Column 5, line 62, "3,5-Di-t-butylmecaptophenol" should read --3,5-Di-t-butylmercaptophenol--;

Column 6, line 28, "calulated" should read --calculated--;

Column 6, line 57, "2-((3,5-di-tert-butylphenyl)thio-b 2-methyl-hexanoic" should read -- 2-((3,5-di-tert-butylphenyl)thio)-2-methyl-hexanoic--;

Column 6, line 59, " : " should read -- ; --;

UNITED STATES PATENT AND TRADEMARK OFFICE
CERTIFICATE OF CORRECTION

PATENT NO. : 4,067,998
DATED : January 10, 1978
INVENTOR(S) : Eugene R. Wagner

It is certified that error appears in the above-identified patent and that said Letters Patent are hereby corrected as shown below:

Column 6, line 66 "2-((3,5-di-tert-butylphenyl)thio-heptanoic acid;" should read -- 2-((3,5-di-tert-butylphenyl)thio)-heptanoic acid; --;

Column 7, line 11 "for period" should read --for a period--;

Column 7, Line 20 "(J. Lab. Clin. Medl; 50: 152 (1957) Clin. Chem., 7,249" should read -- (J. Lab. Clin. Med.; 50: 152 (1957) and Clin. Chem., 7,249 --;

Column 7, line 21 "(1961)." should read -- (1961)). --;

Column 7, line 57 "preverably" should read -- preferably --;

Column 8, line 11 "powered" should read -- powdered --;

Column 8, line 30 "powered" should read -- powdered --;

Column 8, line 64 "described" should read -- describe --;

Column 9, line 25 "defind" should read -- defined --;

Column 9, line 38 "butylphenyl)thio)-b 2-methyl-pentanoic acid" should read --butylphenyl)thio)-2-methyl-pentanoic acid.--;

Column 9, line 57 "$R_3$ represents hydrogen, or a salt thereof formed with" should read -- $R_3$ represents hydrogen -- insert paragraph and continue with --or a salt thereof --;

UNITED STATES PATENT AND TRADEMARK OFFICE
CERTIFICATE OF CORRECTION

PATENT NO. : 4,067,998
DATED : January 10, 1978
INVENTOR(S) : Eugene R. Wagner

It is certified that error appears in the above-identified patent and that said Letters Patent are hereby corrected as shown below:

Column 10, line 5 "pound is 2-((3,5-di-tert-butylphenyl)thio)-b 2-methyl-" should read --pound is 2-((3,5-di-tert-butylphenyl)thio-2-methyl-  --;

Column 10, line 12 "admisistering" should read --administering--;

Column 10, line 33, "whereon" should read --wherein--;

Column 10, line 34, "$R_3 1$ is hydrogen." should read --$R_3$ is hydrogen--;

Column 10, line 43 "metyl" should read --methyl--;

Column 10, line 47 "-butyphenyl)" should read -- -butylphenyl)--

Column 10, line 50 "2-((3,5-di-tert-butylphenyl)thio) heptanoic acid." should read -- 2-((3,5-di-tert-butylphenyl)thio)-2-methyl heptanoic acid. --;

Signed and Sealed this

Thirty-first Day of October 1978

[SEAL]

Attest:

RUTH C. MASON
Attesting Officer

DONALD W. BANNER
Commissioner of Patents and Trademarks